United States Patent
Lovorn et al.

(10) Patent No.: US 10,184,305 B2
(45) Date of Patent: Jan. 22, 2019

(54) ELASTIC PIPE CONTROL WITH MANAGED PRESSURE DRILLING

(71) Applicant: Halliburton Energy Services, Inc., Houston, TX (US)

(72) Inventors: James Randolph Lovorn, Tomball, TX (US); Robello Samuel, Cypress, TX (US); Emad Bakri Yassin Ibrahim, Houston, TX (US)

(73) Assignee: Halliburton Enery Services, Inc., Houston, TX (US)

( * ) Notice: Subject to any disclaimer, the term of this patent is extended or adjusted under 35 U.S.C. 154(b) by 226 days.

(21) Appl. No.: 15/116,328

(22) PCT Filed: May 7, 2014

(86) PCT No.: PCT/US2014/037169
§ 371 (c)(1),
(2) Date: Aug. 3, 2016

(87) PCT Pub. No.: WO2015/171138
PCT Pub. Date: Nov. 12, 2015

(65) Prior Publication Data
US 2017/0009543 A1    Jan. 12, 2017

(51) Int. Cl.
*E21B 21/08*    (2006.01)
*E21B 49/00*    (2006.01)
(Continued)

(52) U.S. Cl.
CPC .............. *E21B 21/08* (2013.01); *E21B 44/00* (2013.01); *E21B 49/003* (2013.01); *E21B 49/08* (2013.01);
(Continued)

(58) Field of Classification Search
CPC .............................. E21B 21/08; E21B 49/003
See application file for complete search history.

(56) References Cited

U.S. PATENT DOCUMENTS 6,484,816 B1 * 11/2002 Koederitz ............... E21B 21/08
175/25
6,904,981 B2 * 6/2005 van Riet .................. E21B 21/08
175/66
(Continued)

FOREIGN PATENT DOCUMENTS

WO    2012106348 A1    8/2012
WO    WO-2013009305 A1    1/2013
WO    WO-2015171138 A1    11/2015

OTHER PUBLICATIONS

"International Application Serial No. PCT/US2014/037169, International Search Report dated Feb. 4, 2015", 3 pgs.
(Continued)

*Primary Examiner* — Kenneth L Thompson
(74) *Attorney, Agent, or Firm* — Chamberlain Hrdlicka

(57) ABSTRACT

Disclosed embodiments include systems and methods for improving the accuracy of bottom hole pressure control. One example embodiment includes a torque and drag model that calculates the elasticity of the drill string, which is included in a managed pressure drilling control system. The addition of the torque and drag calculations provide more accurate surge/swab effect calculations based on pipe movement corrected for elasticity effects. The results of these calculations will be used in a real-time hydraulics model to determine a setpoint pressure which will be utilized by a MPD choke system. Further, the real-time torque and drag models are calibrated to actual hole conditions in real-time using survey, temperature, pressure and downhole tool data to calculate friction factors in a wellbore.

20 Claims, 3 Drawing Sheets

(51) Int. Cl.
*E21B 44/00* (2006.01)
*E21B 49/08* (2006.01)
*G06F 17/11* (2006.01)
*G06F 17/50* (2006.01)
*G01N 9/00* (2006.01)
*G01N 11/00* (2006.01)

(52) U.S. Cl.
CPC .......... *G06F 17/11* (2013.01); *G06F 17/5009* (2013.01); *E21B 2049/085* (2013.01); *G01N 9/00* (2013.01); *G01N 11/00* (2013.01)

(56) References Cited

U.S. PATENT DOCUMENTS

| | | | |
|---|---|---|---|
| 7,054,750 B2 | 5/2006 | Rodney et al. | |
| 7,395,878 B2 * | 7/2008 | Reitsma | E21B 21/08 175/38 |
| 7,836,973 B2 * | 11/2010 | Belcher | E21B 17/042 175/25 |
| 8,347,983 B2 | 1/2013 | Hoyer et al. | |
| 9,051,803 B2 * | 6/2015 | Leuchtenberg | E21B 21/08 |
| 9,279,299 B2 * | 3/2016 | Lovorn | E21B 21/08 |
| 9,646,115 B2 * | 5/2017 | Frydman | G06F 17/5009 |
| 9,879,490 B2 * | 1/2018 | Edbury | E21B 21/08 |
| 2006/0207795 A1 | 9/2006 | Kinder et al. | |
| 2007/0151762 A1 * | 7/2007 | Reitsma | E21B 21/08 175/40 |
| 2007/0227774 A1 * | 10/2007 | Reitsma | E21B 21/08 175/25 |
| 2010/0186960 A1 | 7/2010 | Reitsma et al. | |
| 2011/0139464 A1 | 6/2011 | Henderson et al. | |
| 2013/0146357 A1 | 6/2013 | Lovorn | |

OTHER PUBLICATIONS

"International Application Serial No. PCT/US2014/037169, Written Opinion dated Feb. 4, 2015", 7 pgs.
"Venezuela Application Serial No. 2015-000426, Office Action dated Jun. 13, 2016".

* cited by examiner

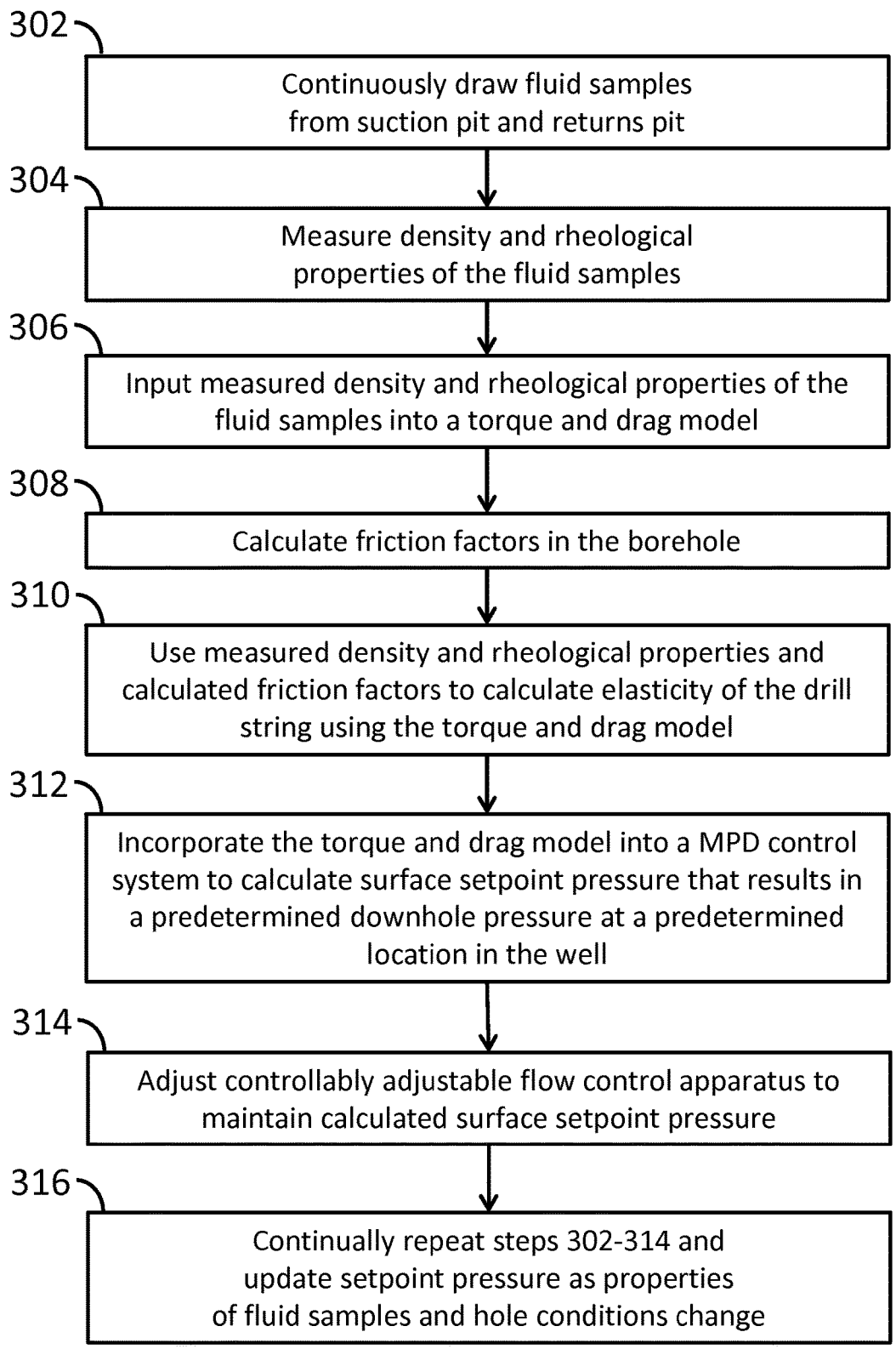

ELASTIC PIPE CONTROL WITH MANAGED PRESSURE DRILLING

PRIORITY APPLICATIONS

This application is a U.S. National Stage Filing under 35 U.S.C. 371 from International Application No. PCT/US2014/037169, filed on 7 May 2014, and published as WO 2015/171138 on 12 Nov. 2015, which is incorporated herein in its entirety.

BACKGROUND

The present disclosure relates generally to systems and methods for bottom hole pressure control.

Earth formations undergo geological changes which result in unexpected pressure and rock strength variations over millions of years. Complex, deep-water and unconventional reservoirs often exhibit wellbore mechanics that prevent use of conventional drilling techniques. Conventional drilling practices have typically maintained the hydrostatic pressure of the drilling fluid in the wellbore between the formation's pore pressure and its fracture pressure. Drilling fluid is continuously circulated within the wellbore to control the formation fluids and transport cuttings to the surface. However, since the drilling fluid pressure is higher than the natural formation pressure, fluid invasion frequently occurs causing permeability damage to the formation, caused by washout of the formation or physical blockage from the intrusion of the fluid into the formation structure itself, resulting in lost circulation of drilling fluid and causing non-productive time.

Managed pressure drilling (MPD) was developed as a group of technologies to more precisely control the annular pressure profile throughout wellbores by creating only a minimal overbalanced annular pressure. MPD involves "low-head" and "at balance" drilling, in which downhole pressure is kept marginally above or equal to the reservoir pore pressure, reducing fluid loss. By ascertaining downhole pressure environmental limits and managing the annular hydraulic pressure profile accordingly, MPD techniques adjust the annular pressure to keep it within desired limits at multiple fixed points in the wellbore while continuously drilling in the wellbore, allowing for drilling through multiple different pore pressure and fracture gradients in the same hole section.

With MPD, there is a need to have precise control on the profile of annular pressure during drilling and cementing. However, current methods using conventional calculations for controlling bottomhole pressures in extended reach wells do not properly take into consideration the elasticity of drill pipes and therefore do not control to the proper pressures. For the foregoing reasons, there is a need for methods of more precisely controlling the annular pressure profile throughout the well bore. By manipulating pressure within the wellbore at multiple depths within the wellbore to better control the annular pressure, several incidents regarding non-productive time can be mitigated, such as differential sticking and lost circulation. MPD also enables possibilities for extending casing points to limit the total number of casings, limiting lost circulation, drilling with total lost returns and increasing the penetration rate.

BRIEF DESCRIPTION OF THE DRAWINGS

FIG. 3 depicts a diagram of an example method of incorporating a torque and drag model that calculates the elasticity of the drill string into the MPD control system.

DETAILED DESCRIPTION

The following detailed description refers to the accompanying drawings that depict various details of examples selected to show how particular embodiments may be implemented. The discussion herein addresses various examples of the inventive subject matter at least partially in reference to these drawings and describes the depicted embodiments in sufficient detail to enable those skilled in the art to practice the invention. Many other embodiments may be utilized for practicing the inventive subject matter than the illustrative examples discussed herein, and many structural and operational changes in addition to the alternatives specifically discussed herein may be made without departing from the scope of the inventive subject matter.

In this description, references to "one embodiment" or "an embodiment," or to "one example" or "an example" mean that the feature being referred to is, or may be, included in at least one embodiment or example of the invention. Separate references to "an embodiment" or "one embodiment" or to "one example" or "an example" in this description are not intended to necessarily refer to the same embodiment or example; however, neither are such embodiments mutually exclusive, unless so stated or as will be readily apparent to those of ordinary skill in the art having the benefit of this disclosure. Thus, the present disclosure includes a variety of combinations and/or integrations of the embodiments and examples described herein, as well as further embodiments and examples as defined within the scope of all claims based on this disclosure, as well as all legal equivalents of such claims.

This disclosure describes systems and methods for improving the accuracy of bottom hole pressure control. One example embodiment includes a torque and drag model that calculates the elasticity of the drill string, which is included in a MPD control system. The addition of the torque and drag calculations provide more accurate surge/swab effect calculations based on pipe movement corrected for elasticity effects. The results of these calculations will be used in a real-time hydraulics model to determine a setpoint pressure which will be utilized by a MPD choke system. Further, the real-time torque and drag models are calibrated to actual hole conditions in real-time using survey, temperature, pressure and downhole tool data to calculate friction factors in a wellbore. When utilizing MPD, the drilling system is a closed loop system which is non-atmospheric. The closed loop is accomplished, for example, by installing a rotating control device (RCD) above a blowout preventer (BOP) at the wellhead.

Figure 1:
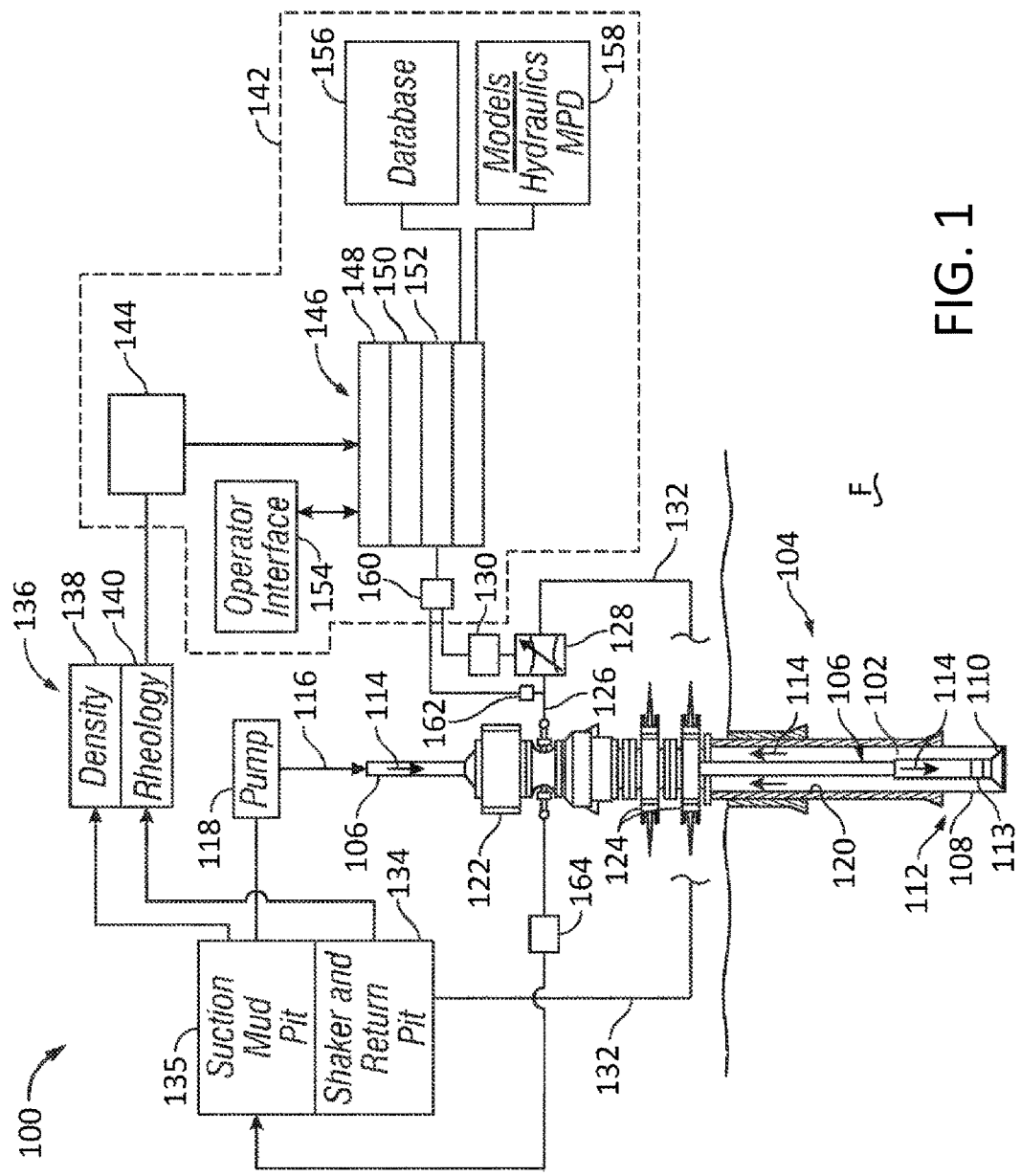
FIG. 1 depicts an example system for controlling wellbore pressure.

FIG. 1 illustrates one example of a drilling system 100 for controlling a wellbore pressure in at least one portion of the annulus 102 of the well 104. A drill string 106 extends down into a wellbore 108, also called a borehole, of the well 104 being drilled through at least one subterranean formation F. The drill string 106 comprises jointed drill pipe sections, which may be of conventional construction, or may be wired pipe sections. The wellbore 108 may be drilled in any direction, for example, vertical, inclined, horizontal, and combinations thereof. A bottomhole assembly (BHA) 112 is coupled at the lower end of the drill string 106, with the BHA terminating with a drill bit 110. The BHA 112 may be of many configurations, but may include, for example, one or more drill collars, as well as other components, such as measurement while drilling and/or logging while drilling tools (MWD/LWD tools) 113, a mud motor, a hole reamer, one or more stabilizers, a steerable drilling assembly, and other suitable tools for drilling a well. Drilling fluid 114 is pumped through input line 116 and into drill string 106 by one or more pumps 118. The drilling fluid 114 travels down the interior of the drill string 102 and exits through the bit 120 into the annulus 102 between the drill string 106 and a wall 120 of the wellbore 108. As the drilling fluid 114 transits up the annulus 102, it picks up drilling cuttings from the drilling of the formation F, which modifies the properties of the drilling fluid 114 due to the presence of the additional material.

In the depicted example, a rotating pressure control device (RCD) 122 allows pressure containment within the wellbore 108 by closing off the annulus 102 between the wellbore 108 and the drill string 106, while still permitting the drill string 106 to advance into the wellbore and to rotate. The RCD 122 is positioned above the blowout preventers (BOP's) 124 at the surface. Drilling fluid 114 circulates out of the wellbore 108 and exits between the BOP's 124 and the RCD 122. Drilling fluid 114 flows through the return line 126 to a controllably adjustable flow control apparatus 128 (also referred to as a controllably adjustable choke) after exiting the wellbore 108. In one example, the controllably adjustable flow control apparatus 128 comprises a controllably adjustable choke valve known in the art, for example the Automated Choke System provided by Halliburton Energy Services, Inc. of Houston, Tex., USA. A restriction to flow through the controllably adjustable choke 128 can be controllably adjusted by an actuator 130 to vary the backpressure in the annulus 102. An operator (or an automated control system) operates the controllably adjustable flow control apparatus 128 to regulate the pressure applied to the annulus at the surface to obtain a desired downhole pressure (DDP). For example, adjustments to a pressure differential across the choke 128 cause a corresponding change in pressure applied to the annulus 102. Thus, a downhole pressure at a predetermined location (e.g., pressure at the bottom of the wellbore 108, pressure at a downhole casing shoe, pressure at a particular formation or zone, etc.) may be regulated by varying the backpressure applied to the annulus 102 at the surface. The actuator 130 is electrically powered, hydraulically powered, and/or pneumatically powered. Downstream of controllably adjustable flow control apparatus 128, drilling fluid 114 returns through line 132 to the return pit 134 where the cuttings are removed. The cleaned drilling fluid 114 is then communicated back to suction pit 135 for another trip through the drill string.

In one embodiment, a real-time system automatically and continually draws fluid samples from the return pit 134 and the suction pit 135 and inputs the samples into a real-time fluid properties testing module 136. The fluid properties testing module 136 comprises a density measurement sensor 138 and a rheology sensor 140. In one example, the density measurement sensor 138 comprises a densometer. In one example, the rheology sensor 140 comprises an in line viscometer to measure properties of the input and output drilling fluid 114. In one example, separate real time fluid properties testing modules 136 are used to test each of the input flow and return flow simultaneously.

Measurements from the sensors 138 and 140 are transmitted to a real-time control system, also called a controller, 142. The controller 142 comprises a data acquisition module 144 for interfacing sensor measurements to an information handling system 146. In one example, the real-time sensor measurements are transmitted to the information handling system (IHS) 146 for use in real-time modeling and control of the controllably adjustable choke 128. For purposes of this disclosure, the IHS 146 comprises any instrumentality, or aggregate of instrumentalities, operable to compute, classify, process, transmit, receive, retrieve, originate, switch, store, display, manifest, detect, record, reproduce, handle, or utilize any form of information, intelligence, measurements, or data for business, scientific, control, and other purposes.

For example, the IHS 146 comprises one or more processing resources such as a central processing unit (CPU) 148, random access memory (RAM) 150, hardware and/or software control logic, one or more disk drives or other storage for containing data and/or operating instructions, read only memory (ROM), and/or other types of nonvolatile memory. For purposes of this disclosure, all such memory devices, whether volatile or non-volatile, and storage drives non-transitory storage devices. In addition, the IHS 146 comprises suitable interface circuits 152 for communicating and receiving data from sensors and/or the data acquisition module 144 at the surface and/or downhole. Additional components of the IHS 146 include one or more network ports for communicating with external devices, as well as various input and output (I/O) devices 154, for example a keyboard, a mouse, and a video display. The IHS 146 also includes one or more buses operable to transmit communications between the various hardware components. A suitable data acquisition module 144 and information handling system 146 for use as described herein in the controller 142 stores information in a database 156 interfaced to the IHS 146. For example, in many systems, the database 156 will include data related to other rig sensors, well geometry, offset well historical data, and/or other drilling fluid parameters used in the real-time models.

In one example, the IHS 146 has programmed instructions, including one, or more, real-time hydraulics software models 158 stored in the memory 150 that when executed transmits control instructions to the controller module 160 to autonomously operate the actuator 130 to control operation of the controllably adjustable choke 128, based, at least in part, on the real-time measured density and rheological properties of the drilling fluid 114. As used herein, the term autonomous is intended to mean automatically, according to programmed instructions, without the requirement for operator input. It should be noted that a manual override may be allowed without departing from the definition of an autonomous system, as used herein. In one example, the controller module 160 is a programmable logic controller that accepts the wellhead pressure setpoint values from the IHS 146 and controls the controllably adjustable choke 128 to maintain that wellhead pressure. While the elements 144, 146, and 160 are depicted separately in FIG. 1, those skilled in the art will appreciate that any, or all, of them could be combined into a single element designated as the controller 142. Alternatively, many of the functions of IHS 146 may be contained in a stand-alone version of controller module 160.

Figure 2:
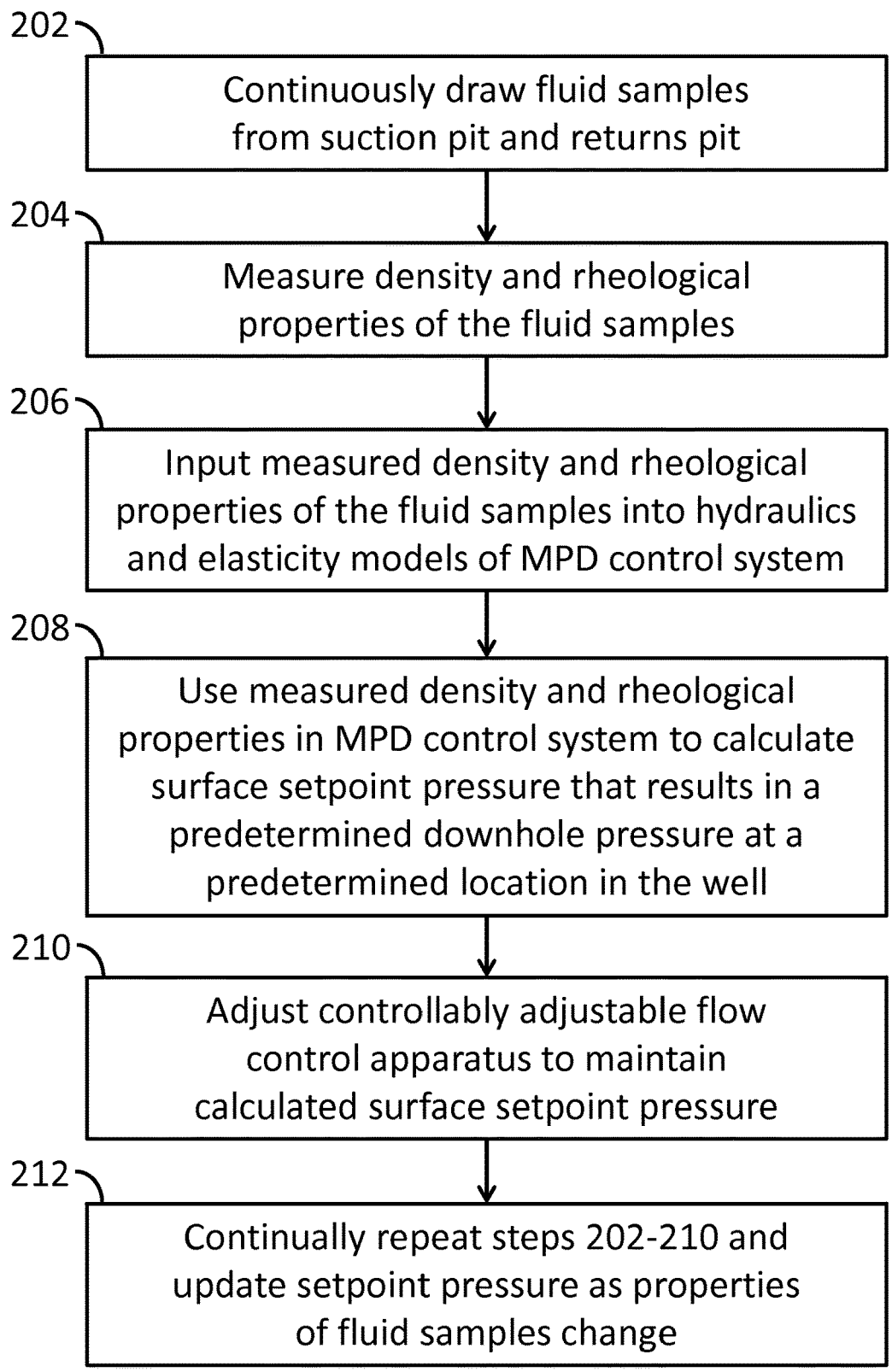
FIG. 2 depicts a diagram of an example method of maintaining a desired downhole pressure.

Referring now to FIG. 2, the figure depicts an example method 200 of using an example MPD control system to maintain a desired downhole pressure at a predetermined location in a wellbore. In the example, a fluid sample is continually drawn from each of the return pit 134 and the suction pit 135 in operation 202. The density and rheological properties of each sample are measured in operation 204, as fluid properties of the drilling fluid such as density and viscosity affect the pressure within the wellbore. In one example, the fluid samples are regulated to a predetermined temperature and pressure before the fluid properties are measured. Rheological properties of interest of the input and return fluids include, but are not limited to: oil/water ratio, density, chlorides content, electric stability, shear stress of the fluid, gel strength, plastic viscosity, and yield point. In one example, shear stress comprises a plurality of shear rates, for example the typical six shear rate settings of common drilling fluid viscometers.

During drilling, it is important to control the pressure within the wellbore ($P_w$) with respect to the pressure within the formation. Traditional drilling practices relied upon maintaining hydrostatic pressure in the annulus to prevent formation fluids from entering the borehole. Ideally, when drilling fluid is circulated down the drill string and up the annulus, an equivalent circulating density (ECD) created is greater than pore pressure ($P_{pore}$), but is below the fracture pressure ($P_{frac}$) necessary to fracture the formation being drilled. The $P_{pore}$ of the formation is the natural pressure of the formation. The $P_{frac}$ of the formation is the pressure at which the drilling fluid fractures and enters the formation. The pressure range above the $P_{pore}$ and below the $P_{frac}$ is referred to as the drilling margin.

Overbalanced drilling (OBD) maintains a relationship between $P_w$ and formation pressure which prevents production fluid from entering the wellbore from the formation (by keeping $P_w$ above $P_{pore}$). Overbalanced conditions within the wellbore are advantageous to control the well and prevent blowouts from occurring, but disadvantages ensue when $P_w$ becomes greater than $P_{frac}$. Specifically, the drilling fluid used when drilling the well bore may fracture and flow into the formation, causing loss of expensive drilling fluid as well as a decrease in productivity of the formation. Conversely, underbalanced drilling (UBD) maintains a relationship between $P_w$ and formation pressure in which allows fluid from exposed formations to flow into the wellbore during drilling operations (by keeping $P_w$ below $P_{pore}$). Underbalanced conditions within the wellbore facilitate production of fluid from the formation to the surface of the wellbore because the higher pressure fluid flows from the formation to the lower pressure area within the wellbore, but the underbalanced conditions may at the same time cause an undesirable blowout or "kick" of production fluid through the wellbore up to the surface of the wellbore. Additionally, if the well is drilled in the underbalanced conditions, production fluids may rise to the surface during drilling, causing loss of production fluid.

Controlling wellbore pressure is difficult due to the nature of fluid flow within the wellbore. Many variables which affect the pressure of drilling fluid within the wellbore exist while drilling, including the motion and effect of the drill string while drilling into the formation, the nature of the formation being drilled, and the increasing equivalent circulation density (ECD) and hydrostatic pressures which accompany increasing depths. The largely unpredictable effects of these variables cause the wellbore pressure to constantly change, especially with increasing depth within the wellbore. With increasing depth within the formation, fluid pressure of drilling fluid within the wellbore correspondingly increases and develops a hydrostatic head, which is affected by the weight of the fluid within the wellbore. The frictional forces caused by the circulation of the drilling fluid between the surface of the wellbore and the deepest portion of the wellbore create an additional pressure within the wellbore termed "friction head." Friction head increases as drilling fluid viscosity increases. The total increase in pressure from the surface of the wellbore to the bottom of the wellbore is the equivalent circulating density (ECD) of the drilling fluid. The pressure differential between ECD within the wellbore and formation pressure at increasing depths can cause the well bore to become overbalanced. The difference between ECD and formation pressure is particularly problematic in extended reach wells, which are drilled to great lengths relative to their depths.

Managed pressure drilling (MPD) is aimed at overcoming drilling problems by using surface pressure to maintain a downhole pressure within the drilling margin that prevents the flow of formation fluids into the wellbore (by keeping $P_w$ above $P_{pore}$) and at the same time prevents drilling fluid from entering the formation (by keeping $P_w$ below $P_{frac}$). MPD operations use the RCD that seals the annular pressure and the choke manifold to create a closed-loop fluid system, wherein sealing or releasing annular pressure at the surface controls downhole pressure in the wellbore. By creating only a minimal overbalanced annular pressure, MPD allows reduced fluid loss and reservoir influx.

In one example, data from operations 202 and 204 relative to fluid properties is imported into the hydraulics model for calculating pressure drops, also called losses, and pressure profiles throughout the closed-loop fluid system. In another example, fluid information and temperature may be manually entered into the hydraulics model. Once the downhole pressure environment has been defined by pore pressures, fracture pressures and wellbore-stability pressures (through the use of real-time measurements, with annular pressure decreases to induce flow or pressure increases to induce losses), MPD is used to maintain an appropriate annular hydraulic pressure profile. Thus MPD allows operators to keep the ECD within a narrow pore-pressure-fracture-gradient window while still maintaining pressures conducive to wellbore stability. This is accomplished primarily through manipulation of backpressure on the annulus while taking into account factors that affect the ECD such as fluid density, fluid rheology, annular fluid velocity, circulating friction and hole geometry. The measured density and rheological properties from operation 204 are input into a hydraulics model and an elasticity model used in a MPD control system, in operation 206. In one example, a hydraulics model is used in the MPD control system, as described more fully below, to calculate pressure losses of the drilling system.

The MPD system calculates a desired surface setpoint pressure using controllably adjustable flow control apparatus that results in a predetermined downhole pressure at a predetermined location in the well, in operation operation 208. In this example system, the MPD system controls annular pressure according to the following equation:

Surface/Well Head Pressure (WHP)=Desired Downhole Pressure (DDP)−Hydrostatic Pressure At Control Point−Fluid Circulating Friction (ECD) At Control Point−Surge/Swab Pressures at Control Point (1)

The described MPD system includes a hydraulics model that calculates the hydrostatic pressures of the fluid based, at least in part, on fluid compressibility, real-time rheology, and thermal effects of the wellbore. Further hydraulics model inputs include geometry inputs such as, for example, survey data, casing/hole section lengths, pipe outer diameter (OD)/inner diameter (ID) measurements and sections, and temperature profiles. These parameters may be manually entered into the model. Such a hydraulics model takes into account changes in the drilling fluid, for example cuttings loading and fluid compressibility, as it transits the flow system in the wellbore. Multiple volumes of drilling fluid, each with different properties, are capable of transiting through the system at any time. The hydraulics model tracks each volume and uses the density and rheological properties associated with each fluid volume to calculate the pressure drops associated with each volume of fluid as they progress through the closed flow system. Pressure drops of the system may comprise pressure losses associated with the surface equipment, the drill string, the BHA, the LWD/MWD tools, the hole reamers, the drill bit, and the annulus. The sum of the pressure losses provides a calculated standpipe pressure. The hydraulics model generates a pressure profile in the well annulus that may be compared to the well pore pressure and fracture pressure at desired locations along the well.

In this example system, the hydraulics model calculates surge/swab pressures based, at least in part, on a form of Hershel-Bulkley's surge/swab calculations to control the bottomhole pressures. Drill string tripping causes additional pressure variations in the borehole. Movement of the drill string when pulling out of the borehole will cause pressures of the drilling fluid on the bottom of the hole to decrease due to friction between the movement of the pipe and the drilling fluid. This is referred to as swab pressure ($P_{swab}$). Conversely, movement of the drill string of running in the borehole will cause pressure to increase. This is referred to as surge pressure ($P_{surge}$). $P_{swab}$ and $P_{surge}$ friction pressures impact displacement of fluid caused by drill string movement (piston effect) in a fluid-filled borehole. High surge and swab pressures may lead to lost circulation or the influx of formation fluid, resulting in undesireable well control challenges.

The MPD system further includes an elasticity model that compensates for pressure variations due to drill pipe movement by incorporating a torque and drag model to calculate the elasticity of the drill string. Pipe movement is not homogeneous or in a steady state due to factors such as wellbore tortuosity. This is due to the elasticity of the pipe, fluid and mechanical force coupling. Thus, the velocity at the pipe end is not necessarily equal to the velocity imposed at the surface, with portions of the pipe that accelerate and de-accelerate at different speeds. Further, pipe in the drill string may be in tension and compression at the same time.

In this example system, the elasticity model performs wellbore pressure calculations caused by pipe movement inside the wellbore based on an analysis of fluid flow and pipe motion. The elasticity model preferably solves the full balance of mass and balance of momentum for pipe and annulus flow, considering the compressibility of the fluids, the elasticity of the system, and the dynamic motions of pipes and fluids. Also considered are surge pressures related to fluid column length below the moving pipe, compressibility of the formation, and axial elasticity of the moving string. Fluid properties are adjusted to reflect the effects of pressure and temperature on the fluids.

Elasticity model calculations are divided into two regions: the interval from the surface to the end of the pipe and the interval from the end of the pipe to bottomhole. In the upper region, pipe pressures are coupled to annulus pressures through the radial elasticity of the pipe. The axial dynamic response of the tubular string is given by the following set of equations:

$$\text{Momentum equation: } \rho * A * \partial v / \partial t = \partial F / \partial x \quad (2)$$

$$\text{Linear elasticity equation: } \partial F / \partial t = A * E * \partial v / \partial x \quad (3)$$

Where
v=velocity
$\rho$=density
A=cross sectional area
E=Young's modulus
x=length
t=time Methods such as the Bergeron Method, Finite Element Method (Galerkin Procedure), or interpolated method of characteristics may be used to solve the fluid flow and pipe dynamics of the Pipe-Annulus and Pipe-To-Bottomhole regions described above. For a fixed time step, this method requires that the algebraic equations be solved only once. For each additional time step, the equations only need to be evaluated. The maximum time step allowed is the minimum grid spacing divided by the sonic velocity. For a drill string near bottomhole, the minimum grid spacing is the distance off bottom. In order to avoid very small time-step sizes for surges near bottomhole, a "near bottomhole" element is defined for this special case that neglects inertia. The fluid flow and pipe velocity equations are solved subject to the boundary conditions given above. For non-linear boundary conditions, the equations are solved using the Newtonian and non-Newtonian models. The calculation uses the hole section, fluid, wellpath, workstring, and other parameters such as acceleration/deceleration of the pipe, pipe speed.

The Pipe-to-Bottomhole region, along with the Coupled Pipe-Annulus region, are connected through a set of force and displacement compatibility relations. These relations include: (a) elastic force in the moving pipe is equal to the pressure below the pipe times the pipe end area. This means that a sufficiently high pressure below the pipe could retard the pipe motion; (b) mass flow balances are calculated for flow through the pipe nozzle, flow through the annulus return area, flow into the pipe-to-bottomhole region, and fluid displaced by the pipe; (c) pressure drops are calculated through the pipe nozzle and annulus return area based on cross-sectional area changes with appropriate discharge coefficients; and (d) boundary conditions for a float option are chosen to allow one-way flow through the float. The float refers to a non-return valve in the drill string (e.g., one way valve) that creates a closed system (as opposed to open system). Fluid is allowed to flow out of the float; otherwise the float is treated as a closed pipe. Surface boundary conditions set the fluid pressures in the tube and the annulus to atmospheric pressure. The bottomhole boundary condition assumes a rigid floor, which requires a zero-fluid velocity.

The calculated WHP setpoint pressure in the MPD system is then transmitted from the hydraulics model and the elasticity model to the controller module. The controller module directs the actuator to adjust the controllably adjustable choke to achieve a wellhead pressure approximately equal to the calculated setpoint pressure. As indicated above, the calculated setpoint pressure imparts a surface pressure on the annulus such that results in the DDP at a predetermined location along the annulus. As indicated above, in one example, the DDP comprise a predetermined pressure in a range that is less than the fracture pressure and greater than, or equal to, the pore pressure of the surrounding formation F. Determining set point pressures for MPD choke systems allows for drilling through and completing complex pore and fracture pressure regimes, improved drilling efficiency due to reduced drilling risk, and avoids installation of multiple, expensive casing strings in the wellbore.

The controllably adjustable flow control apparatus is adjusted to maintain the calculated surface pressure, in operation 210. As changes to real-time density and rheological properties of the drilling fluid are detected, the new values are inputted into the real-time hydraulics model and elasticity model. The real-time hydraulics model and elasticity model calculations are repeated, the pressure losses are recalculated, and a modified controllably adjustable flow control apparatus set point is calculated, and transmitted to controller to adjust the surface pressure to achieve the desired downhole pressure at the predetermined location. In one example, back pressure pump may be used to help maintain the calculated WHP, for example when there is little or no flow of drilling fluid. There is a continual two-way transfer of data and information between the MPD control system and the data acquisition module and controller through IHS. The data acquisition module and IHS operate to maintain a continual flow of real-time data from the sensors to the MPD control system, so that the hydraulics model and the elasticity model have the information they need to adapt to changing circumstances, and to update the desired wellhead setpoint pressure that results in a predetermined pressure at a predetermined downhole location. The hydraulics model and elasticity model of the MPD control system operate to supply the controller continually with a real-time value for the desired wellhead setpoint pressure that results in the desired downhole pressure at the predetermined location. Lastly, the sequence is continually repeated and the setpoint adjusted as the properties of the fluid samples change in operation 212.

FIG. 3 depicts an example method of incorporating a torque and drag model that calculates the elasticity of the drill string into the MPD control system. In the example, a fluid sample is continually drawn from each of the return pit and the suction pit in operation 302. The density and rheological properties of each sample are measured in operation 304. The measured density and rheological properties are input into in a torque and drag model in operation 306. The torque and drag model is calibrated to actual hole conditions in real-time using surveys, temperature, pressure and downhole tool data to calculate friction factors in the borehole. The friction factors in the borehole are calculated in operation 308. The torque and drag model calculates elasticity of the drill string, in operation 310. The torque and drag model is incorporated into the MPD control system to calculate a desired surface setpoint pressure at the controllably adjustable flow control apparatus that results in a predetermined downhole pressure at a predetermined location in the well, in operation 312. The controllably adjustable flow control apparatus is adjusted to maintain the calculated surface pressure, in operation 314. The sequence is periodically repeated and the setpoint adjusted as the properties of the fluid samples and as downhole conditions change, in operation 316. In many systems, the sequence may be repeated essentially continuously, at least while drilling is occurring; but may also be performed at selected intervals. Additionally, in some examples, some properties or factors may be determined at different intervals than other properties or factors.

While the processes described herein is described as autonomous, so that no human interaction is required to control the setpoint pressure, human intervention may be used, if desired.

In one embodiment, the present disclosure may be embodied as a set of instructions on a computer readable medium comprising ROM, RAM, CD, DVD, hard drive, flash memory device, or any other computer readable medium, now known or unknown, that when executed causes an IHS, for example IHS 146, to implement a method of the present disclosure, for example the method described in FIGS. 2-3.

Though described serially in the examples of FIGS. 2-3, one of ordinary skill in the art would recognize that other examples may reorder the operations, omit one or more operations, and/or execute two or more operations in parallel using multiple processors or a single processor organized as two or more virtual machines or sub-processors. Moreover, still other examples can implement the operations as one or more specific interconnected hardware or integrated circuit modules with related control and data signals communicated between and through the modules. Thus, any process flow is applicable to software, firmware, hardware, and hybrid implementations.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
    obtaining at least one fluid property of an input fluid to a well and of a return fluid from the well;
    calculating an elasticity parameter of a drill string within the well based at least in part on the at least one fluid property;
    calculating a wellhead setpoint pressure that results in a predetermined downhole pressure at a predetermined location in the well, the calculation based at least in part on the elasticity parameter and the at least one fluid property; and
    controllably regulating the flow of the return fluid to maintain the calculated wellhead setpoint pressure.

2. The method of claim 1, wherein the at least one fluid property comprises at least one of: fluid density, oil/water ratio, chlorides content, electric stability, shear stress of the fluid, gel strength, plastic viscosity, yield point, and combinations thereof.

3. The method of claim 1, wherein calculating the elasticity parameter further comprises using a torque and drag model to calculate the elasticity of the drill string.

4. The method of claim 3, further comprising calibrating the torque and drag model to conditions within the well.

5. The method of claim 1, further comprising calculating at least one friction factor present within the well.

6. The method of claim 1, wherein obtaining at least one fluid property comprises withdrawing a sample of the input fluid and the return fluid and regulating a temperature and a pressure of each sample to a predetermined temperature and a predetermined pressure before obtaining the at least one fluid property.

7. The method of claim 1, wherein the predetermined downhole pressure is in a range that is less than a fracture pressure and greater than, or equal to, a pore pressure of a formation surrounding the well.

8. The method of claim 1, wherein the predetermined downhole pressure is less than a pore pressure of a formation surrounding the well.

9. A method for controlling a downhole pressure during drilling comprising:
- periodically sensing in real-time at least one fluid property of an input fluid into a well and of a return fluid from the well;
- inputting the at least one fluid property into of a drilling control system;
- calculating in real-time, using the drilling control system, a wellhead setpoint pressure that results in a predetermined downhole pressure at a predetermined location in the well, the calculation based at least in part on the at least one fluid property and an elasticity model of the well incorporating the at least one fluid property; and
- controllably regulating the flow of the return fluid to maintain the calculated wellhead setpoint pressure.

10. The method of claim 9, wherein the drilling control system includes a hydraulics model incorporating the at least one fluid property.

11. The method of claim 9, wherein the at least one fluid property comprises at least one of: fluid density, oil/water ratio, chlorides content, electric stability, shear stress of the fluid, gel strength, plastic viscosity, yield point, and combinations thereof.

12. The method of claim 9, wherein continuously sensing the at least one fluid property comprises withdrawing a sample of the input fluid and the return fluid and regulating a temperature and a pressure of each sample to a predetermined temperature and a predetermined pressure before obtaining the at least one fluid property.

13. The method of claim 9, wherein the predetermined downhole pressure is in a range that is less than a fracture pressure and greater than, or equal to, a pore pressure of a formation surrounding the well.

14. The method of claim 9, wherein the predetermined downhole pressure is less than a pore pressure of a formation surrounding the well.

15. A drilling system for managed pressure drilling, comprising:
- at least one sensor configured to continually sense at least one fluid property of an input fluid to a well and a return fluid from the well;
- a controllably adjustable flow control apparatus disposed in a return flow line to regulate a flow of the return fluid; and
- a controller operably connected to the controllably adjustable flow control apparatus to instruct the controllably adjustable flow apparatus to regulate the flow of the return fluid to maintain a wellhead setpoint pressured based at least in part on an elasticity model of the well incorporating the at least one fluid property.

16. The drilling system of claim 15, wherein the controller comprises a processor in data communication with a memory, the memory containing programmed instruction that when executed calculates a surface wellhead setpoint pressure that results in a desired downhole pressure at a predetermined location, where the calculated wellhead setpoint pressure is based at least in part on the sensed fluid property.

17. The drilling system of claim 15 wherein the programmed instructions further comprise a hydraulics model of the well.

18. The drilling system of claim 15, wherein the controller acts autonomously to adjust the controllably adjustable flow control apparatus to regulate the flow of the return fluid to maintain the calculated wellhead setpoint pressure.

19. The drilling system of claim 15, wherein the at least one sensor comprises at least one first sensor in hydraulic communication with the input fluid and at least one second sensor in hydraulic communication with the return fluid.

20. The drilling system of claim 15, wherein the at least one sensor further comprises at least one first sensor positioned in the well configured to measure a downhole condition.

* * * * *